(12) United States Patent
Kang (10) Patent No.: US 12,016,706 B2
(45) Date of Patent: Jun. 25, 2024

(54) NOTIFICATION METHOD FOR CONTINUOUS BLOOD GLUCOSE MONITORING SYSTEM

(71) Applicant: I-SENS, INC., Seoul (KR)

(72) Inventor: Bo Weol Kang, Seoul (KR)

(73) Assignee: I-SENS, INC., Seoul (KR)

( * ) Notice: Subject to any disclaimer, the term of this patent is extended or adjusted under 35 U.S.C. 154(b) by 173 days.

(21) Appl. No.: 17/628,563

(22) PCT Filed: Mar. 13, 2020

(86) PCT No.: PCT/KR2020/003519
§ 371 (c)(1),
(2) Date: Jan. 20, 2022

(87) PCT Pub. No.: WO2021/025255
PCT Pub. Date: Feb. 11, 2021

(65) Prior Publication Data
US 2022/0361825 A1    Nov. 17, 2022

(30) Foreign Application Priority Data
Aug. 8, 2019  (KR) .................. 10-2019-0096652

(51) Int. Cl.
*A61B 5/00* (2006.01)
*A61B 5/145* (2006.01)

(52) U.S. Cl.
CPC .......... *A61B 5/746* (2013.01); *A61B 5/0022* (2013.01); *A61B 5/14503* (2013.01); *A61B 5/14532* (2013.01); *A61B 5/742* (2013.01)

(58) Field of Classification Search
CPC ... A61B 5/746; A61B 5/0022; A61B 5/14503; A61B 5/14532; A61B 5/742;
(Continued)

(56) References Cited

U.S. PATENT DOCUMENTS

2008/0088467 A1*  4/2008  Al-Ali ............... A61B 5/14551
                                                        702/182
2014/0200426 A1   7/2014  Taub et al.
2018/0360314 A1* 12/2018  Wang .................... G16H 50/30

FOREIGN PATENT DOCUMENTS

EP    3 721 790      10/2020
JP    2010-506625    3/2010
(Continued)

OTHER PUBLICATIONS

International Preliminary Report on Patentability (Chapter I) for PCT/KR2020/003519 dated Feb. 8, 2022 and its English translation from WIPO (now published as WO 2021/025255).
(Continued)

*Primary Examiner* — Omar Casillashernandez
(74) *Attorney, Agent, or Firm* — Ladas & Parry, LLP (57) ABSTRACT

The present disclosure relates to a notification method of a continuous glucose monitoring system. A notification method of a continuous glucose monitoring system, according to one embodiment of the present invention, may comprise the steps of: performing a communication connection between a body attachment unit and a communication terminal for the communication terminal to receive blood glucose data measured from the body attachment unit which is attached to a human body and continuously measures blood glucose; transmitting information on the body attachment unit from the body attachment unit to the communication terminal and calculating a remaining use period of the body attachment unit; and generating, in the communication terminal, a notification on the remaining use period of the body attachment unit. According to the present disclosure, as the notification for the remaining period of the body attachment unit is generated in the communication terminal, there is an effect wherein a user can prepare in advance a body (Continued)

attachment unit to be replaced before the use period of the body attachment unit ends.

9 Claims, 5 Drawing Sheets

(58) Field of Classification Search
CPC ...... A61B 2560/0271; A61B 2560/028; A61B 5/6849; A61B 5/0024; A61B 5/7235; A61B 5/7275; G16H 40/63; G16H 40/67
USPC ........................................................ 340/540
See application file for complete search history.

(56) References Cited

FOREIGN PATENT DOCUMENTS

| | | |
|---|---|---|
| JP | 2017-123093 | 7/2017 |
| JP | 2018-000303 | 1/2018 |
| JP | 2019-510388 | 4/2019 |
| KR | 10-2009-0079940 | 7/2009 |
| KR | 10-0985630 | 10/2010 |
| WO | 2017/040700 | 3/2017 |

OTHER PUBLICATIONS

Office Action dated Nov. 1, 2022 for Japanese Patent Application No. 2022-505472 and its English translation from Global Dossier.
Office Action dated Jan. 19, 2021 for Korean Patent Application No. 10-2019-0096652 and its English translation from Global Dossier.
Notice of Allowance dated Aug. 13, 2021 for Korean Patent Application No. 10-2019-0096652 and its English translation from Global Dossier.
Examination Report No. 1 dated May 16, 2023 for Australian Patent Application No. 2020324822.
Extended European Search Report dated Jun. 27, 2023 for European Patent Application No. 20849305.6.
International Search Report for PCT/KR2020/003519 dated Jun. 22, 2020 and its English translation from WIPO (now published as WO 2021/025255).
Written Opinion of the International Searching Authority for PCT/KR2020/003519 dated Jun. 22, 2020 and its English translation by Google Translate (now published as WO 2021/025255).
Examination Report No. 1 dated Sep. 5, 2023 for New Zealand Patent Application No. 784075.

* cited by examiner

NOTIFICATION METHOD FOR CONTINUOUS BLOOD GLUCOSE MONITORING SYSTEM

CROSS-REFERENCE TO RELATED APPLICATIONS

The present application is the U.S. National Phase of PCT Application No. PCT/KR2020/003519 filed on Mar. 13, 2020, which claims the priority to Korean Patent Application No. 10-2019-0096652 filed on Aug. 8, 2019, the entire contents of which are incorporated herein by reference.

TECHNICAL FIELD

The present disclosure is generally related to a notification method for a continuous blood glucose monitoring system, in more detail, a notification method for a continuous blood glucose monitoring system notifying to a user a use status related to a sensor module included in a body attachable unit configured to be attachable to a human body and measure blood glucose.

BACKGROUND

Diabetes is a major cause of death and a cause of disability worldwide, and therefore, many people have health problems due to diabetes. Specially, diabetes is a serious disease that causes heart and kidney disease, blindness, nerve damage and high blood pressure. According to a long-term clinical study, the incidence of complications can be significantly reduced by appropriately managing blood glucose levels. Therefore, it is important to continuously manage diabetes, an important factor is self-monitoring of blood glucose levels.

In response to this demand, a self-diagnosis biometer in which a user can check a blood glucose level of the user by himself or herself has been widely distributed and used. A conventional blood glucose meter measures the blood glucose level of the user by putting the user's blood on a sensor strip, which is a test strip. Accordingly, the sensor strip with the blood is inserted into the blood glucose meter, and the blood glucose level measured through the sensor strip is displayed on the blood glucose meter.

At this time, the blood glucose meter receives an electrical signal generated by an electrochemical reaction between the collected blood and the reactant in the sensor strip, and measures the blood glucose level. Such a finger prick method helps diabetic patients to manage blood glucose, but it is difficult to accurately identify the blood glucose levels which are being frequently changed because it shows only the result at the time of the measurement.

Diabetics patients generally experience hyperglycemia and hypoglycemia, an emergency may occur in the hypoglycemic conditions, and the patients may become unconscious or die if a hypoglycemic condition lasts for an extended period of time without the supply of sugar. Accordingly, although rapid discovery of the hypoglycemic condition is critically important for diabetics, blood-collecting type glucose monitoring devices intermittently measuring glucose have limited ability to accurately measure blood glucose levels.

To overcome such a drawback, continuous glucose monitoring systems (CGMSs) inserted into the human body to measure a blood glucose level every few minutes have been developed, and therefore easily perform the management of diabetics and responses to an emergency situation.

The continuous blood glucose monitoring system comprises a body attachable unit for being inserted into the human body, collecting test substance such as blood of a user, and measuring blood glucose, and a communication terminal for communicating with the body attachable unit and displaying a blood glucose level measured by the body attachable unit. The body attachable unit cannot be used permanently and has life of a certain time period, so, when the usable time period is expired, it needs to be replaced.

If the usable time period is expired, the body attachable unit does not measure the blood glucose of the body on the expiration time, and does not perform the transmission of the data to the communication terminal. Depending on cases, the power of the body attachable unit may be automatically turned off.

Accordingly, because the user cannot receive the blood glucose data from the body attachable unit anymore if the usable time period of the body attachable unit ends, the user needs to replace the body attachable unit, but, since the user does not know a precise time point in which the usable time period of the body attachable unit ends, there is a problem of being uncapable of timely replacing the body attachable unit.

DETAILED DESCRIPTION OF DISCLOSURE

Technical Problem

The solve the problems of the conventional art, the purpose of the present disclosure is for providing a notification method for a continuous blood glucose monitoring system notifying a remaining usable time period of a body attachable unit to a user so that the body attachable unit with a limited usable time period can be replaced at an appropriate time.

Additionally, another purpose of the present disclosure is for providing a notification method for a continuous blood glucose monitoring system preventing reconnection and reuse of a body attachable unit of which usable time period is expired.

Solution to Problem

A notification method according to an embodiment of the present disclosure may comprise: connecting communication between a body attachable unit and a communication terminal such that blood glucose data measured by the body attachable unit configured to be attachable to a body and continuously measure blood glucose is received by the communication terminal; transmitting information of the body attachable unit from the body attachable unit to the communication terminal and calculating a remaining usable time period of the body attachable unit; and generating notification regarding the remaining usable time period of the body attachable unit on the communication terminal.

The calculating of the remaining usable time period of the body attachable unit may comprise calculating the remaining usable time period of the body attachable unit based on information of a time point in which the body attachable unit is activated and information of a preset usable time period of the body attachable unit, which are transmitted from the body attachable unit to the communication terminal.

The notification regarding the remaining usable time period of the body attachable unit may be generated when a notification generation time point set at the communication terminal is reached.

The notification method may further comprise, by checking whether blood glucose data which has not been received from the body attachable unit exists before the preset usable time period of the body attachable unit is expired, receiving, by the communication terminal, the blood glucose data, which has not been received from the body attachable unit, from the body attachable unit.

The notification method may further comprise: determining, by the communication terminal, whether communication of the body attachable unit is disconnected; when the communication terminal determines that the communication of the body attachable unit is disconnected, transmitting, from the communication terminal to a server, information of a communication disconnection time point of the body attachable unit, information of a time point in which the body attachable unit is activated, and information of a preset usable time period of the body attachable unit; and verifying, by the server, the communication disconnection time point of the body attachable unit, wherein the verifying of the communication disconnection time point of the body attachable unit is performed using whether an actual use time period of the body attachable unit matches the preset usable time period of the body attachable unit.

The determining of whether the communication of the body attachable unit is disconnected may comprise, if the communication terminal does not receive the blood glucose data from the body attachable unit for a set time period, determining that the communication of the body attachable unit is disconnected.

The verifying of the communication disconnection time point of the body attachable unit may comprise: calculating the actual use time period of the body attachable unit using the time point in which the body attachable unit is activated and the communication disconnection time point of the body attachable unit; and verifying the communication disconnection time point of the body attachable unit using whether the calculated actual use time period of the body attachable unit matches the preset usable time period of the body attachable unit.

The notification method may further comprise, if the calculated actual use time period of the body attachable unit does not match the preset usable time period of the body attachable unit, transmitting, from the server to the communication terminal, a notification indicating that blood glucose data which has not been received from the body attachable unit exists.

The notification method may further comprise, if the notification indicating that the blood glucose data which has not been received from the body attachable unit exists is transmitted from the server to the communication terminal, reconnecting, by the communication terminal, communication with the body attachable unit and receiving blood glucose data, stored at the body attachable unit, from the body attachable unit.

The notification method may further comprise, if the preset usable time period of the body attachable unit is expired when the communication terminal reconnects the communication with the body attachable unit, maintaining a state that power of the body attachable unit is turned off, and not measuring, by the body attachable unit, the blood glucose data.

Advantageous Effects of Invention

According to the present disclosure, a communication terminal outputs a notification regarding a remaining usable time period of a body attachable unit, and therefore there is an advantageous technical effect in that a user can prepare a new body attachable unit with which the body attachable unit is replaced in advance before a usable time period of the body attachable unit ends.

Depending on cases, when there is data which has not been transmitted to a communication terminal among blood glucose data measured by a body attachable unit, the communication between the body attachable unit and the communication terminal are temporarily reconnected to receive blood glucose data stored at the body attachable unit, and accordingly there is an advantageous technical effect of preventing missing blood glucose data.

Further, when outputting the notification regarding the remaining usable time period of the body attachable unit, the communication terminal can display information on how to purchase a body attachable unit, and therefore there is an advantageous technical effect in that the user can conveniently purchase a body attachable unit.

DESCRIPTION OF EMBODIMENTS OF DISCLOSURE

The technical terms used in the present disclosure are only for the purpose of describing exemplary embodiments, and they are not intended to limit the present invention. Also, unless otherwise defined, all technical terms used herein should be construed as having the same meaning as commonly understood by those skilled in the art, and should not be interpreted as being excessively inclusive or excessively restrictive. In addition, when a technical term used herein is an erroneous technical term that does not accurately represent the idea of the present invention, it should be understood as replacing the term by a technical term which can be properly understood by those skilled in the art.

Further, singular expressions used in the present specification include plural expressions unless they have definitely opposite meanings. In the present application, it shall not be construed that terms, such as "including" or "comprising", various constituent elements or steps described in the specification need to be all essentially included, and it shall be construed that some constituent elements or steps among the various constituent elements or steps may be omitted, or additional constituent elements or steps may be further included.

Also, it should be noted that the accompanying drawings are merely illustrated to easily explain the spirit of the invention, and therefore, they should not be construed to limit the spirit of the invention by the accompanying drawings.

Hereinafter, with reference to the enclosed drawings, a method for notifying a remaining usable period of a continuous blood glucose monitoring system according to an embodiment of the present disclosure is described in detail.

Figure 1:
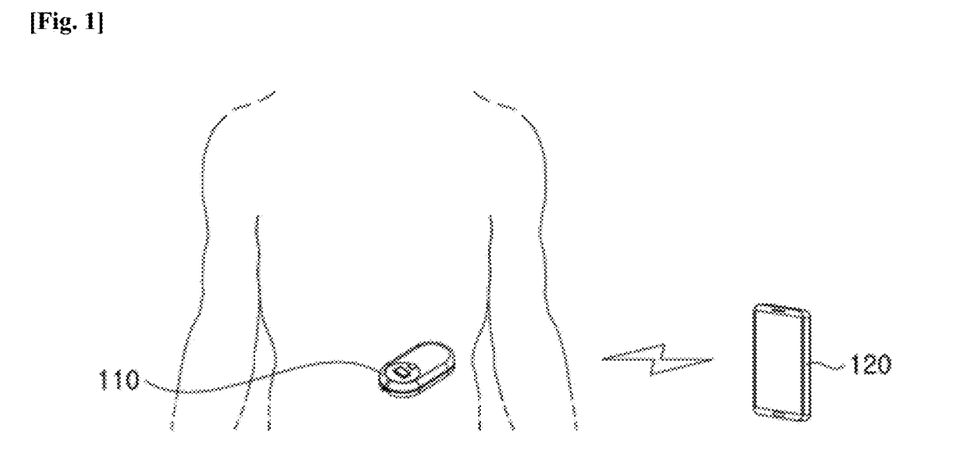
FIG. 1 is a schematic diagram for illustrating a continuous blood glucose monitoring system according to an embodiment of the present disclosure.

FIG. 1 is a schematic diagram for illustrating a continuous blood glucose monitoring system according to an embodiment of the present disclosure.

Referring to FIG. 1, the continuous blood glucose measurement system according to an embodiment of the present disclosure comprises a body attachable unit (110) and a communication terminal (120).

The body attachable unit (110) is attachable to human body and, when the body attachable unit (110) is attached to the human body, an end portion of a sensor of the body attachable unit (110) is inserted into skin to periodically extract body fluid of the human body and measure blood glucose.

The communication terminal (120) is a terminal configured to receive blood glucose information from the body attachable unit (110) and output or display the received blood glucose information to a user, and for example, the communication terminal (120) may be a portable terminal (such as smartphone, tablet PC, or notebook and so on) configured to communicate with the body attachable unit (110). However, the communication terminal (120) is not limited thereto, and may be any type of a terminal which has a communication function and program or application can be installed to.

The body attachable unit (110) transmits the blood glucose information in response to request of the communication terminal (120) or at predetermined times periodically, and for data communication between the body attachable unit (110) and the communication terminal (120), the body attachable unit (110) and the communication terminal (120) are communicationally connected to each other over a wire by an USB cable and so on or communicationally connected in an wireless communication means such as infrared communication, NFC communication, Bluetooth, etc.

Figure 2:
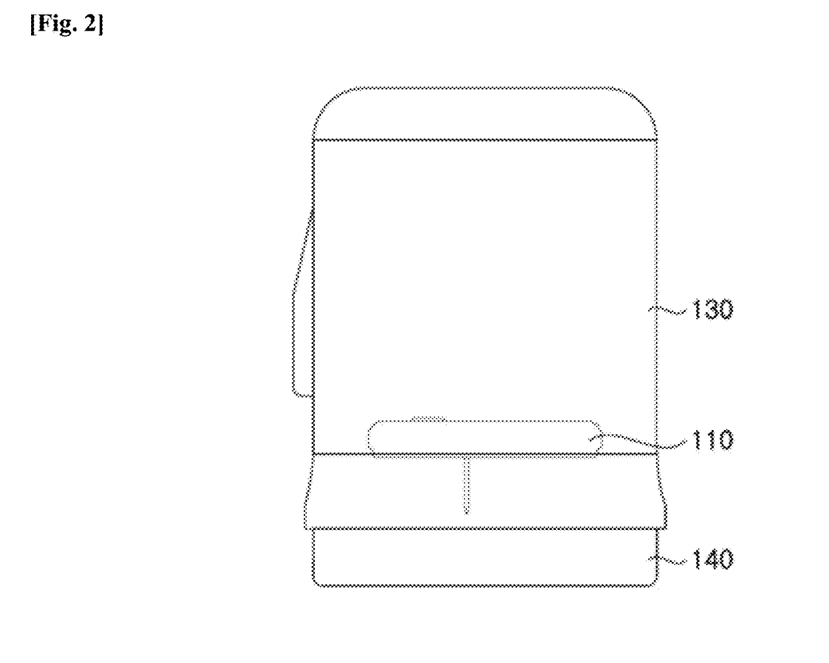
FIG. 2 is a figure illustrating an applicator for attaching a body attachable unit to a part of a human body according to an embodiment of the present disclosure.
Figure 3:
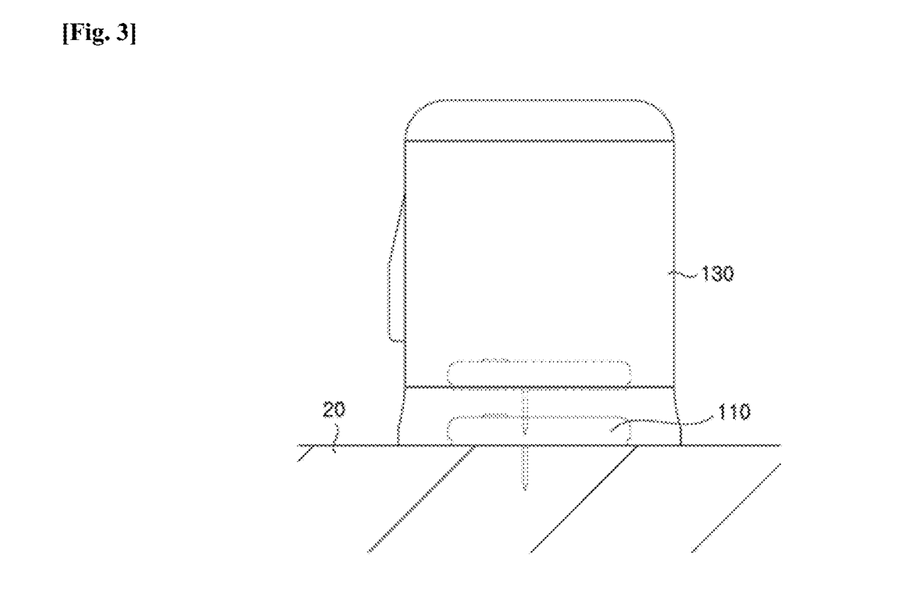
FIGS. 3 and 4 are figures for illustrating a process of attaching a body attachable unit to a human body using an applicator according to an embodiment of the present disclosure.
Figure 4:
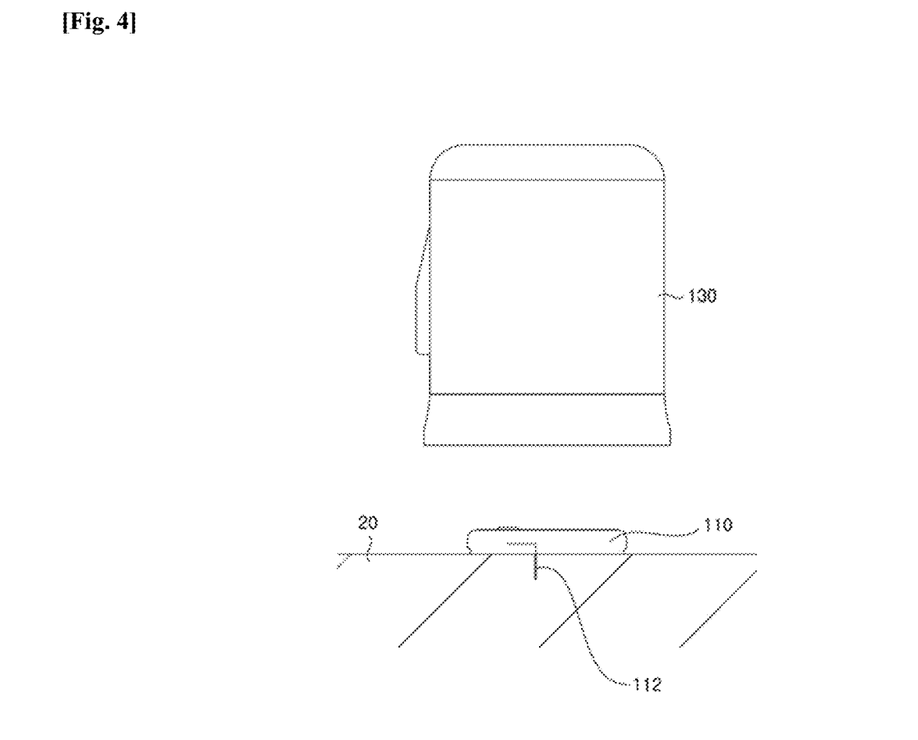

The body attachable unit (110) is attached to a part of the human body by an applicator, FIG. 2 is a figure illustrating an applicator for attaching a body attachable unit to a part of a human body according to an embodiment of the present disclosure, and FIGS. 3 and 4 are figures for illustrating a process of attaching a body attachable unit to a human body using an applicator according to an embodiment of the present disclosure.

Firstly, an application (130) is now described by referring to FIG. 2, the body attachable unit (110) is mounted in the applicator (130), and the applicator (130) can be operated so that the body attachable unit (110) can be outwardly discharged to the outside of the applicator (130) by the manipulation of the user and then be attached to a specific portion of the human body of the user. The applicator (130) is formed to have a shape that one side of the applicator (130) is open, and the body attachable unit (110) is installed to the applicator (130) through the open side of the applicator (130).

When the body attachable unit (110) is attached to a part of the human body using the applicator (130), for inserting an end portion of the sensor included in the body attachable unit (110) to skin, the applicator (130) comprises a needle (not shown) formed to cover the end portion of the sensor therein, a first elastic means (not shown) pushing the needle and the end portion of the sensor together towards the skin, and a second elastic means (not shown) configured to retract the needle only. The compressed state of the first elastic means (not shown) arranged to be compressed inside the applicator (130) by the configuration of the applicator (130) can be released, thereby inserting the needle and the end portion of the sensor simultaneously to the skin, and when the end portion of the sensor is inserted to the skin, the compressed state of the second elastic means (not shown) is released, thereby extracting the needle only. By the applicator (130), the user can safely and easily attach the body attachable unit (110) to the skin.

A process of attaching the body attachable unit (110) to the human body will be described in detail with reference to FIGS. 3 and 4, in a state that a protection cap (140) is separated or removed, an open side of the applicator (130) is closely placed on a specific part of skin (20) of the human body. When the applicator (130) is operated in a state that the applicator (130) is closely placed on the skin (20) of the human body, the body attachable unit (110) is outwardly discharged from the applicator (130) and then attached to the skin (20). Here, an end portion of the sensor (112) is arranged to be exposed from the body attachable unit (110) at a lower portion of the body attachable unit (110), and a part of the end portion of the sensor (112) is inserted into the skin (20) by a needle installed at the applicator (130). Accordingly, the body attachable unit (110) can be attached to the skin (20) in a state that an end portion of the sensor (112) is inserted to the skin (20).

In the embodiment of the present disclosure, an adhesive tape is provided at a surface of the body attachable unit (110) contacting the human body so that the body attachable unit (110) can be attached to the skin (20). Accordingly, if the applicator (130) is moved away from the skin (20) of the human body, the body attachable unit (110) is fixedly attached to the skin (20) of the human body by the adhesive tape.

After that, if the power is supplied to the body attachable unit (110), the body attachable unit (110) is communicationally connected with the communication terminal (130), and the body attachable unit (110) transmits the measured blood glucose information to the communication terminal (120).

The body attachable unit (110) can measure not only the blood glucose information but also various biometric information, and hereinafter blood glucose information is illustrated as one of examples of biometric information.

Figure 5:
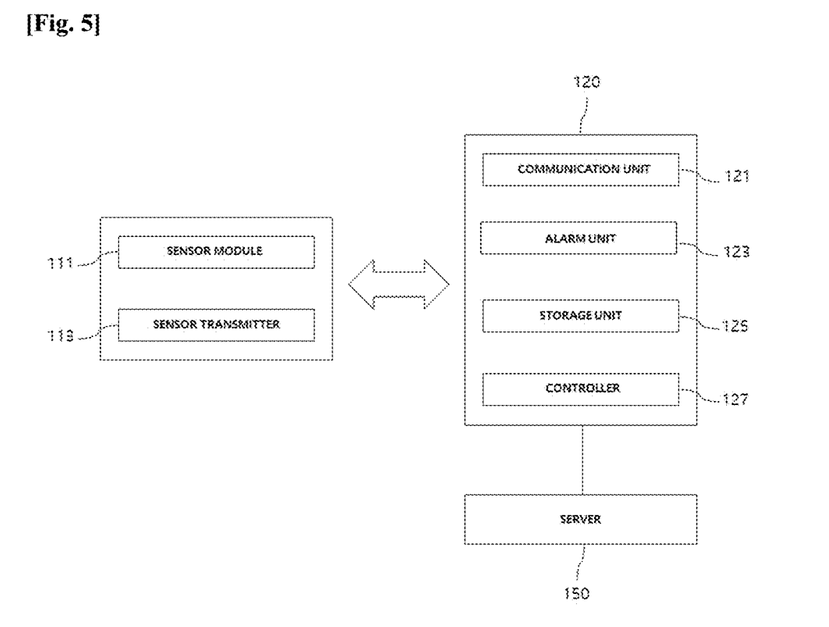
FIG. 5 is a block diagram for illustrating a continuous blood glucose monitoring system according to an embodiment of the present disclosure.

FIG. 5 is a block diagram for illustrating a continuous blood glucose monitoring system according to an embodiment of the present disclosure.

Referring to FIG. 5, a continuous blood glucose monitoring system (1100) according to an embodiment of the present disclosure comprises a body attachable unit (110), a communication terminal (120) and a server (150).

The body attachable unit (110) is attached to the human body in order to extract the body fluid of the human body and periodically measure blood glucose, and transmits the measured blood glucose data to the communication terminal (120).

The communication terminal (120) communicates with a sensor transmitter of the body attachable unit (110), and receives information associated with or related to the body attachable unit (110) from the sensor transmitter (113). The communication terminal (120) can receive identification or unique information, such as identifier information and serial number information of the body attachable unit (110), information about time point of starting communication between the body attachable unit (110) and the communication terminal (120) (e.g. activation time of the body attachable unit (110)), and useable period information of the body attachable unit (110) and blood glucose data measured by the sensor module (111).

And, the communication terminal (120) calculates a remaining usable period of a body attachable unit by receiving information associated with or related to the body attachable unit (110). The calculated remaining usable period of the body attachable unit (110) can be notified to the user to warn the user.

The server (150) can communicate with the communication terminal (120), and at the time of disconnection or termination of communication of the body attachable unit (110), inspection is performed. Accordingly, when there is an error at the time of disconnection or termination of communication of the body attachable unit (110), the server (150) notifies to the communication terminal (120) that there is an error at the time of disconnection or termination of communication.

Detailed configuration of the body attachable unit (110) will be described. The body attachable unit (110) comprises a sensor module (111) and a sensor transmitter (113).

The sensor module (111) monitors the blood glucose of the human body for a time period of approximately one (1) week to one hundred twenty (120) days. In this embodiment, the usable time period of the sensor module (111) can be limited to a certain time period, such as about one (1) week, fifteen (15) days, thirty (30) days, or one hundred twenty (120) days. When the usable period of the sensor module (111) is expired, the blood glucose measurement or monitor is not performed any more even though the body attachable unit (110) is attached to the human body. In the present embodiment, the body attachable unit (110) and the applicator (130) can be configured to be one time disposable.

A part of a sensor included in the sensor module (111) can be inserted into a human body, and the sensor comprises a distal portion, a body, and a proximal portion. The blood glucose information measured by the distal portion can be transferred to the sensor transmitter through a tracer of the body and an electronic pad arranged to the proximal portion. The sensor transmitter (113) transforms the blood glucose information transmitted from the sensor module (111) to a digital signal and stores it, and transmits the stored blood glucose data to the communication terminal (120).

According to the present disclosure, the blood glucose data stored at the sensor transmitter (113) may be blood glucose data measured by the sensor module (111) for twelve (12) hours. At that time, the blood glucose data stored at the sensor transmitter (113) can be blood glucose data measured for a certain time period among blood glucose data measured by the sensor module (111). Alternatively, the blood glucose data stored to the sensor transmitter (113) can be deleted after a certain time period passes and recent data is stored.

The sensor transmitter (113) transmits blood glucose data measured by the sensor module (111) to the communication terminal (120), and transmits the information of the body attachable unit (110) to the communication terminal (120). At that time, the information from the sensor transmitter from the sensor transmitter (113) to the communication terminal (120) can be identification or unique information of the body attachable unit (110), such as an identifier and a serial number of the body attachable unit (110) and information on a time point in which the body attachable unit (110) is activated and a useable time period of the body attachable unit (110).

Next, detailed configurations of the communication terminal (120) will be described. The communication terminal (120) comprises a communication unit (121), an alarm unit (123), a storage unit (125) and a controller (127).

The communication unit (121) can communicate with the sensor transmitter (113) of the body attachable unit (110), and receive information associated with or related to the body attachable unit (110) from the sensor transmitter (113). At that time, the information regarding the body attachable unit (110) received by the communication unit (121) can be identification or unique information of the body attachable unit (110), such as an identifier and a serial number of the body attachable unit (110) and information on a time point in which the body attachable unit (110) is activated and a usable time period of the body attachable unit (110). Additionally, the communication unit (121) receives the blood glucose data measured by the body attachable unit (110).

At the present embodiment, the communication unit (121) can perform wireless communication with the sensor transmitter (113), and the wireless communication can be near field communication or mobile communication or wifi communication.

And, the communication unit (121) can communication with the server (150), and the communication between the communication unit (121) and the server (150) can be performed through a mobile communication network or a wifi communication network. Alternatively, the communication between the communication unit (121) and the server (150) can be performed through the internet network.

The alarm unit (123) can be configured to notify, to the user, information regarding remaining usable period of the body attachable unit (110). The alarm unit (123) can be a display device of the communication terminal (120) or a speaker which is capable of outputting a sound and the like, and can be a vibrator configured to vibrate the communication terminal (120).

The alarm unit (123) can output an alarm regarding a remaining usable time period to the user at a predetermined time. For example, the alarm unit (123) can output an alarm regarding the remaining usable time period by displaying it on a display device of the communication terminal (120) before three (3) days, one (1) day, twelve (12) hours, one (1) hour and so on from the use expiration time of the body attachable unit (110). And, if necessary, the alarm unit (123) can output a sound from a speaker and activate the operation of the vibrator at the time of displaying on the display device in order to generate the alarm.

Additionally, the alarm unit (123) can continuously display the remaining usable time period of the body attachable unit (110) on the display device of the communication terminal (120).

The storage unit (125) store information of a user of the communication terminal (120). The communication terminal (120) can store the information of the user authenticated through a log-in process by executing a program or application stalled to the communication terminal (120). At that time, the information of the user can be an ID, name and birthdate of the user and so on.

The controller (127) can control the communication unit (121), the alarm unit (123) and the storage unit (125), and calculate the remaining usable time period of the body attachable unit (110) using information received from the body attachable unit (110). And, the controller (127) stores the calculated remaining usable time period to the storage unit (125), and controls the alarm unit (123) so that the alarm can be outputted at a predetermined time.

At that time, if the communication terminal (120) is communicationally connected with the body attachable unit (110), the controller (127) receives information on a time in which the body attachable unit (110) is activated and an whole usable period of the body attachable unit (110) and calculates a remaining usable time period of the body attachable unit (110) at the current time based on the received information. And, the controller (127) continuously checks whether a preset alarm output time is reached. When the alarm output time is reached, the controller (127) can control the alarm unit (123) to output an alarm of a remaining usable time period of the body attachable unit (110) to the user by the communication terminal (120).

And, at the time when the remaining usable time period of the body attachable unit (110) ends, the controller (127) checks whether there is blood glucose data which has not been received from the body attachable unit (110). At that time, if the usable time period of the body attachable unit (110) expires, the power of the body attachable unit (110) can be turned off, and therefore the blood glucose data can be received from the body attachable unit (110) anymore. Accordingly, if blood glucose data not received from the body attachable unit (110) exists before the usable time period of the body attachable unit (110) expires, the communication terminal (120) requests and receives the blood glucose data which has not been received from the body attachable unit (110).

However, a case in which, before the usable time of the body attachable unit (110) ends normally, the communication terminal (120) does not receive blood glucose data from the body attachable unit (110) may occur. When the controller (127) does not receive the blood glucose data from the body attachable unit (110) for a preset time period continuously, the controller (127) determines that the operation of the body attachable unit (110) is discontinued, and transmits, to the server (150), information about an operation termination time point.

An example in which the controller (127) determines as the termination/discontinuation operation of the body attachable unit (110) is a normal case that blood glucose data cannot be received from the body attachable unit (110) anymore due to the expiration of the usable time period of the body attachable unit (110). In the meanwhile, another example in which the controller (127) determines as the termination/discontinuation operation of the body attachable unit (110) is an abnormal case that blood glucose data cannot be received continuously for a preset time period due to the disconnection of the communication between the body attachable unit (110) and the communication terminal (120) even though the remaining usable time period of the body attachable unit (110) is still left.

Accordingly, the verification about the operation termination/discontinuation time point of the body attachable unit (110) is needed to determine whether the operation of the body attachable unit (110) is normally terminated due to the expiration of the usable time period of the body attachable unit (110) or the operation of the body attachable unit (110) is abnormally terminated because of the disconnection of the communication between the body attachable unit (110) and the communication terminal (120).

The controller (127) receives a verification result regarding the operation termination/discontinuation time point of the body attachable unit (110) from the server (150), and, when based on the verification result the controller (127) determines that the operation of the body attachable unit (110) is normally terminated due to the expiration of the usable time period of the body attachable unit (110), a normal message can be received. In this case, the controller (127) controls to maintain a state of disconnection of the communication between the communication terminal (120) and the body attachable unit (110).

However, when based on the verification result the controller (127) determines that the operation of the body attachable unit (110) is abnormally terminated because of the disconnection of the communication between the body attachable unit (110) and the communication terminal (120) even though the remaining useable time period is still left, an abnormal message can be received.

When receiving the abnormal message, the controller (127) can control the communication unit (121) to reconnect the communication with the body attachable unit (110) to receive, from the body attachable unit (110), blood glucose data which has not been received due to the communication disconnection during the remaining useable time period. Accordingly, the blood glucose data stored at the body attachable unit (110) can be received through the communication unit (121) by the communication terminal (120). At that time, the blood glucose data received by the communication terminal (120) from body attachable unit (110) can be blood glucose data which has not been transmitted to the communication terminal (120), or if necessary, all blood glucose data stored at the body attachable unit (110).

As described above, the controller (127) controls to end the reconnection of the communication with the body attachable unit (110) if receiving the unreceived blood glucose data from the body attachable unit (110).

A process of performing the verification regarding the operation termination/discontinuation time of the body attachable unit (110) will be described in further detail. The server (150) receives identification or unique information of the body attachable unit (110), such as an identifier and serial number of the body attachable unit (110), and information about a time point of activation of the body attachable unit (110), a usable time period of the body attachable unit (110), and a time point of termination of the operation of the body attachable unit (110).

Accordingly, the server (150) can calculate time in which the body attachable unit (110) has been actually used using activation time of the body attachable unit (110) and operation termination time of the body attachable unit (110). By comparing the calculated actual use period of the body attachable unit (110) with a useable time period of the body attachable unit (110), the server (150) can verify whether the operation of the body attachable unit (110) is normally terminated normally or terminated abnormally due to the communication disconnection.

If the actual use period of the body attachable unit (110) is different from the preset usable time period, the server (150) can determine that the operation of the body attachable unit (110) is ended abnormally because of the communication disconnection, and determine that blood glucose data which was not transmitted to the communication terminal (120) among blood glucose data measured by the body attachable unit (110) exists. Accordingly, the server (150) can transmit, to the communication terminal, an alarm notifying that blood glucose data not transmitted to the communication terminal (120).

Figure 6:
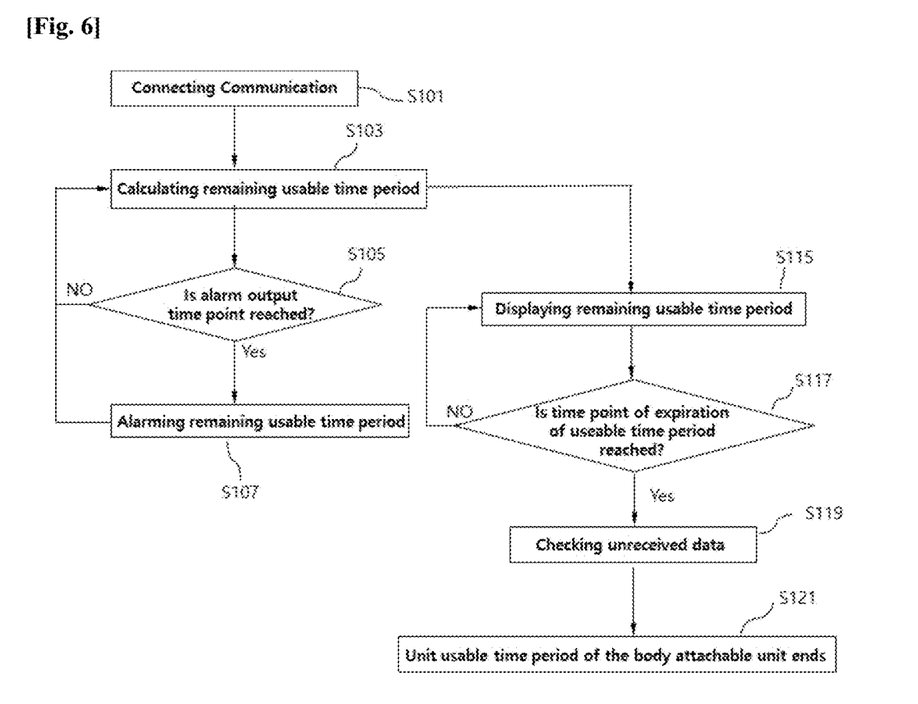
FIG. 6 is a flowchart for illustrating a notification method of a continuous blood glucose monitoring system according to an embodiment of the present disclosure.
Figure 7:
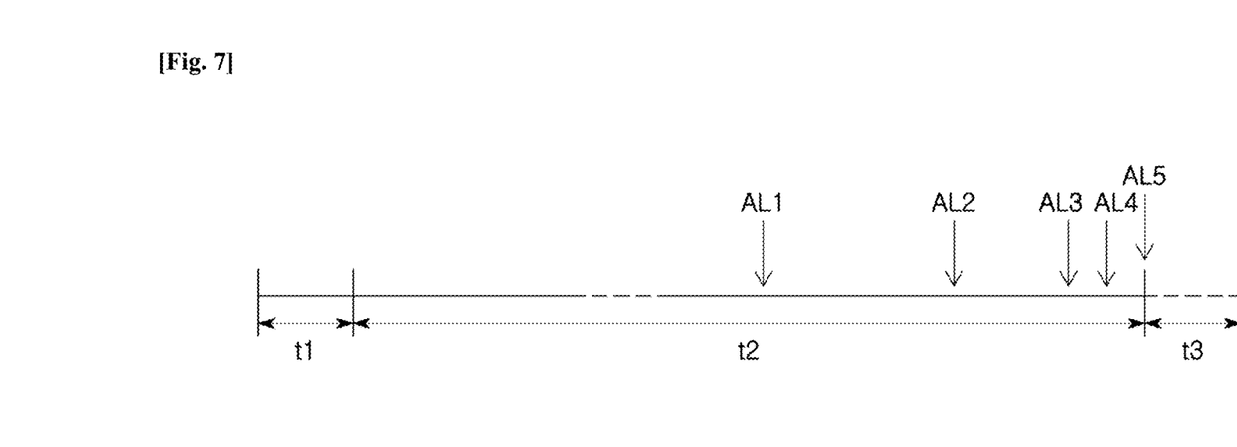
FIG. 7 is a graph for illustrating a notification method of a continuous blood glucose monitoring system according to an embodiment of the present disclosure.

FIG. 6 is a flowchart for illustrating a notification method of a continuous blood glucose monitoring system according to an embodiment of the present disclosure, and FIG. 7 is a graph for illustrating a notification method of a continuous blood glucose monitoring system according to an embodiment of the present disclosure.

Referring to FIG. 6 together with FIGS. 1 to 5, a notification method of a continuous blood glucose monitoring system (100) will be described.

The communication terminal (120) performs communication connection with the body attachable unit (110) (S101). If the communication terminal (120) is communicationally connected to the body attachable unit (110), the communication terminal (120) receives information associated with or related to the body attachable unit (110) from the body attachable unit (110). At that time, the information received from the body attachable unit (110) by the communication terminal (120) may be identification or unique information of the body attachable unit (110), such as an identifier and serial number of the body attachable unit (110), information regarding an activation time point of the body attachable unit (110), and information regarding use information of the body attachable unit (110).

Additionally, the communication terminal (120) receives the blood glucose data measured by the body attachable unit (110). The blood glucose data is measured by the body attachable unit (110), and can be transmitted from the body attachable unit (110) to the communication terminal (120) in real time or periodically.

If the communication terminal (120) is communicationally connected to the body attachable unit (110), the communication terminal (120) calculates a remaining useable time period of the body attachable unit (110) using the information associated with or related to the body attachable unit (110) received from the body attachable unit (110) (S103). The remaining useable time period of the body attachable unit (110) can be calculated using information regarding a time point in which the body attachable unit (110) is activated and information of a usable time period. Accordingly, the communication terminal (120) can calculate the remaining usable time period of the body attachable unit (110) by calculating an actual use time period which is from an activation time point of the body attachable unit (110) to a current time in which blood glucose information is received and subtracting the actual use time period from the useable time period of the body attachable unit (110).

At that time, referring to FIG. 7, when the body attachable unit (110) is attached to the human body, stabilization may be performed for a certain time period (t1). For example, the stabilization of the body attachable unit (110) may take about one (1) to three (3) hours. This stabilization time may be time for needing to stably measure blood glucose at the human body by the sensor (112) because one end portion of the sensor (112) is inserted into the human body. The stabilization may be performed every time when the body attachable unit (110) is attached to the human body.

And, the transmission of the blood glucose data from the body attachable unit (110) to the communication terminal (120) can be performed for the stabilization time (t1). However, the communication terminal (120) can only receive the blood glucose data received for the stabilization time (t1), but may not output it to the user. Accordingly, the time period for outputting the blood glucose data on the communication terminal (120) may be a time period (t2) from a time of ending the stabilization time of the body attachable unit (110) to a time of expiring the useable time period.

And, the predetermined useable time period of the body attachable unit (110) may be time period which is the sum of the stabilization time (t1) and the data receipt period (t2). For example, when time period in which the blood glucose data is being displayed is fifteen (15) days and the stabilization time period is two (2) hours, the preset useable time period of the body attachable unit (110) may be fifteen (15) days and two (2) hours.

Additionally, the time point in which the body attachable unit (110) is activated is a time point in which power starts to be supplied to the body attachable unit (110) attached to the human body, and the stabilization time period (t1) starts from the time point in which the body attachable unit (110) is activated.

The communication terminal (120) performs the calculation of the remaining useable time period of the body attachable unit (110), and checks whether the preset alarm output time point is reached (S105). The checking of whether the preset alarm output time point is reached is a step for checking whether time points (AL1 to AL5) for generating alarms regarding the remaining usable time period are reached. For example, the preset alarm output time point may be, for example, three (3) days, one (1) day, one (1) hour before the expiration of the useable time period, and the alarm indicates the remaining usable time period of the body attachable unit (110).

Accordingly, when the time point for outputting the alarm is reached, the communication terminal (120) generates or outputs the alarm regarding the remaining usable time period of the body attachable unit (110) (S107). At that time, the alarm regarding the remaining usable time period can be generated or outputted by displaying the remaining usable time period on a display device or generating sound or vibration. As illustrated in FIG. 7, the alarm of the remaining usable time period can be outputted multiple times until the expiration of the useable time period of the body attachable unit (110), and the intervals of outputting the alarms can be shorter as the expiration of the useable time period of the body attachable unit (110) comes closer.

In addition, according to the present embodiment, the communication terminal (120) can generate or output an alarm of recommending preparing new body attachable unit (110) together with the alarm related to the remaining usable time period. And, if necessary, on the display device, the communication terminal (120) can provide an URL link for purchasing new body attachable unit (110). Therefore, the user can access an online market site through the URL link for purchasing new body attachable unit (110), displayed on the communication terminal (120), and purchase new body attachable unit (110) at the accessed online market site.

At that time, the communication terminal (120) can display an URL link in which a same body attachable unit (110) can be purchased using information related to the body attachable unit (110), which the user is currently using, based on identification or unique information of the body attachable unit (110), such as an identifier and serial number of the body attachable unit (110).

Meanwhile, if the communication terminal (120) completes the calculation of the remaining usable time period of the body attachable unit (110) (S103), the remaining usable time period of the body attachable unit (110) is displayed on the communication terminal (120) (S115).

At that time, the output of the remaining usable time period of the body attachable unit (110) on the communication terminal (120) can be continuously displayed, although not limited thereto. For instance, information regarding the remaining usable time period of the body attachable unit (110) can be displayed on the communication terminal (120) only when the user is executing the program or the application of the communication terminal (120) in a state that the communication between the body attachable unit (110) and the communication terminal (120) is connected.

And, the communication terminal (120) checks whether a time point of expiration of the useable time period of the body attachable unit (110) is reached (S117). When the time point of expiration of the useable time period of the body attachable unit (110) is not reached, the communication terminal (120) outputs or displays the remaining usable time period of the body attachable unit (110).

When the time point of expiration of the useable time period of the body attachable unit (110) is reached, the communication terminal (120) checks whether blood glucose data which has not been received from the body attachable unit (110) exists (S119), and then the useable time period of the body attachable unit (110) ends or is expired (S121). If the useable time period of the body attachable unit (110) ends, the communication terminal (120) cannot receive the blood glucose data from the body attachable unit (110) anymore because the the power of the body attachable unit (110) is turned off.

Accordingly, according to the present disclosure, by checking, by the communication terminal (120), whether blood glucose data which has not been received from the body attachable unit (110) exists, the communication terminal (120) can receive all blood glucose data from the body attachable unit (110) before the useable time period of the body attachable unit (110) ends.

Additionally, as described above, by notifying the remaining usable time period of the body attachable unit (110) to the user, the reuse of the body attachable unit (110) of which useable time period is expired can be prevented.

Figure 8:
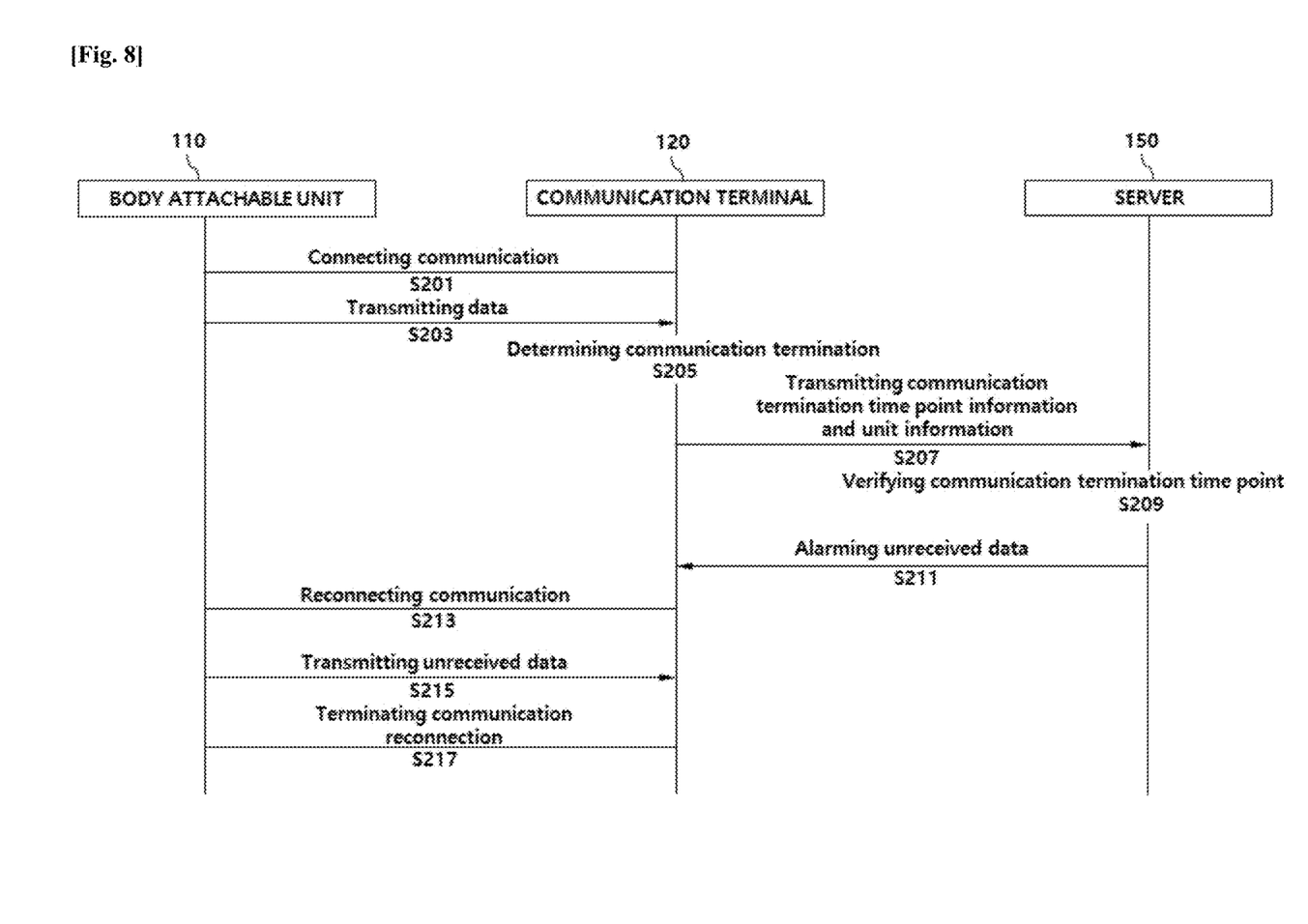
FIG. 8 is a flowchart of illustrating a notification method of a continuous blood glucose monitoring system according to another embodiment of the present disclosure.

FIG. 8 is a flowchart of illustrating a notification method of a continuous blood glucose monitoring system according to another embodiment of the present disclosure.

Referring to FIG. 8, a notification method of a continuous blood glucose monitoring system (100) according to another embodiment of the present disclosure will be described. When describing another embodiment, the duplicate descriptions which are the same as or similar to the embodiments described above are omitted. And, another embodiment is described referring to FIGS. 1 to 7.

According to the present embodiment, the communication terminal (120) performs the communication connection with the body attachable unit (110) to receive blood glucose data from the body attachable unit (110) (S201). When the communication terminal (120) completes the communication connection to the body attachable unit (110), the communication terminal (120) receives information related to or associated with the body attachable unit (110) from the body attachable unit (110). At this step, the information received from the body attachable unit (110) by the communication terminal (120) is identification or unique information of the body attachable unit (110), such as an identifier and a serial number of the body attachable unit (110), information about a time point of activation of the body attachable unit (110), and a useable time period of the body attachable unit (110).

When the communication terminal (120) is communicationally connected with the body attachable unit (110), the communication terminal (120) receives blood glucose data from the body attachable unit (110) (S203). The blood glucose data can be periodically transmitted from the body attachable unit (110) to the communication terminal (120).

At that time, the body attachable unit (110) can have the time for stabilization, as described above, the stabilization time is time of being consumed for stably monitoring or measuring blood glucose by a sensor inserted into the human body, and it can take around one (1) to three (3) hours. The communication terminal (120) may not display the received blood glucose data during the stabilization time period. And, when the stabilization time period of the body attachable unit (110) ends, the received blood glucose data can be displayed.

A case in which the communication terminal (120) does not receive the blood glucose data from the body attachable unit (110) before the usable time period of the body attachable unit (110) is expired may occur. If the communication terminal (120) does not receive the blood glucose data from the body attachable unit (110) for a preset time period continuously, the communication terminal (120) determines that the operation of the body attachable unit (110) is stopped (S205).

The case in which the body attachable unit (110) is operated described above can be a case that the blood glucose data cannot be received from the body attachable unit (110) anymore because the usable time period of the body attachable unit (110) is expired, and this is a normal case that the operation of the body attachable unit (110) is terminated normally.

However, a case in which the blood glucose data cannot be received for a preset time period continuously due to disconnection of the communication between the body attachable unit (110) and the communication terminal (120) even though the remaining usable time period of the body attachable unit (110) is still left may occur, and this is an abnormal case that the operation of the body attachable unit (110) ends abnormally.

Accordingly, it is needed to verify whether the operation of the body attachable unit (110) is terminated normally due to the expiration of the usable time period of the body attachable unit (110) or whether the operation of the body attachable unit (110) is terminated abnormally because of the disconnection of the communication between the body attachable unit (110) and the communication terminal (120). At that time, a time point when the operation of the body attachable unit (110) is termination can be checked to verify whether the termination of the operation of the body attachable unit (110) is normal or abnormal.

Therefore, the communication terminal (120) transmits information on the time point of the termination of the operation of the body attachable unit (110) and the information related to or associated with the body attachable unit (110) to the server (150) in order to verify the time point of the termination of the operation of the body attachable unit (110) (S207).

And, the server (150) performs the verification regarding the time point of the termination of the operation of the body attachable unit (110) using identification or unique information of the body attachable unit (110) (such as a serial number of the body attachable unit (110)), information on a time point of activation of the body attachable unit (110), and information on a usable time period of the body attachable unit (110) and a time point of the termination of the operation of the body attachable unit (110) (S209).

The verification regarding the time point of the termination of the operation of the body attachable unit (110) by the server (150) will be described. The server (150) can calculate a time period in which the body attachable unit (110) is actually used using the time point of the activation of the body attachable unit (110) and the time point of the termination of the operation of the body attachable unit (110). The server (150) can verify whether the operation of the body attachable unit (110) is terminated normally, or abnormally due to the communication disconnection, by comparing the actually used time period of the body attachable unit (110) with the preset usable time period of the body attachable unit (110).

If the actually used time period of the body attachable unit (110) does not match with the preset usable time period of the body attachable unit (110), the server (150) determines that the operation of the body attachable unit (110) ends abnormally due to the communication disconnection, and recognizes that blood glucose data which has not been transmitted to the communication terminal (120) among the blood glucose data measured by the body attachable unit (110) exists. Accordingly, the server (150) can transmit, to the communication terminal (120), an alarm for notifying that there is blood glucose data which has not been transmitted to the communication terminal (120) (S211).

If the communication terminal (120) receives, from the server (150), the alarm regarding the existence of the unreceived data, the communication terminal (120) performs the reconnection of the communication with the body attachable unit (110) (S215).

At that time, if it is a case that the usable time period of the body attachable unit (110) is not expired, a state of the power of the body attachable unit (110) is maintained to be turned on and the body attachable unit (110) continues to measure the blood glucose data, and therefore the measured blood glucose data is transmitted to the communication terminal (120). Additionally, the body attachable unit (110) can also transmit blood glucose data which has not been transmitted to the communication terminal (120).

Depending on cases, when receiving the alarm because of passing the preset time from the time point of the termination of the operation of the body attachable unit (110), the usable time period of the body attachable unit (110) may be already expired. According to the present embodiment, even though the usable period of the body attachable unit (110) is expired, a state that the power is not turned off and the power is turned on for a certain time period can be maintained. Like this, when the usable time period of the body attachable unit (110) is expired, the blood glucose of the human body is not measured even though the state that the power of the body attachable unit (110) is turned on is maintained.

Accordingly, when the preset useable time period (t1+t2) is expired, the body attachable unit (110) does not measure the blood glucose data. However, in this case, as illustrated in FIG. 7, the body attachable unit (110) can maintain a state that the power of the body attachable unit (110) is turned on for a certain time period (t3).

When the communication between the body attachable unit (110) and the communication terminal (120) is reconnected by the alarm during the certain time period (t3), the blood glucose data not transmitted is transmitted to the communication terminal (120) (S217). At this step, the blood glucose data transmitted from the body attachable unit (110) to the communication terminal (120) may be blood glucose data which has not been transmitted to the communication terminal (120). Alternatively, because the body attachable unit (110) stores blood glucose data for about recent twelve (12) hours among blood glucose data measured by the body attachable unit (110), all data stored at the body attachable unit (110) can be transmitted to the communication terminal (120).

As described above, if all unreceived blood glucose data is transmitted from the body attachable unit (110) to the communication terminal (120) by reconnecting the communication between the body attachable unit (110) and the communication terminal (120), the reconnected communication between the body attachable unit (110) and the communication terminal (120) is terminated (S219). At this step, the termination of the reconnected communication of the body attachable unit (110) and the communication terminal (120) can be terminated by ending, by the communication terminal (120), the communication connection with the body attachable unit (110).

As described above, the foregoing detailed descriptions regarding the present disclosure have been presented by way of exemplary embodiments, but the detailed exemplary embodiments are presented as preferred examples, and therefore it should be understood that the present disclosure shall not be limited to those exemplary embodiments, and the scope of the present disclosure shall be defined by the Claims and all of their equivalents fall within the scope of the present disclosure.

What is claimed is:

1. A notification method, comprising
connecting communication between a body attachable unit and a communication terminal;
determining whether the communication between the body attachable unit and the communication terminal is disconnected;
when it is determined that the communication between the body attachable unit and the communication terminal is disconnected, transmitting, from the communication terminal, information of a communication disconnection time point of the body attachable unit, information of a time point in which the body attachable unit is activated, and information of a usable time period of the body attachable unit; and
verifying the communication disconnection time point of the body attachable unit,
wherein the verifying of the communication disconnection time point of the body attachable unit is performed using whether an actual use time period of the body attachable unit matches the usable time period of the body attachable unit.

2. The notification method according to claim 1, further comprising:
transmitting information of the body attachable unit from the body attachable unit to the communication terminal and calculating a remaining usable time period of the body attachable unit; and
generating notification regarding the remaining usable time period of the body attachable unit on the communication terminal,
wherein the calculating of the remaining usable time period of the body attachable unit comprises calculating the remaining usable time period of the body attachable unit based on the information of the time point in which the body attachable unit is activated and the information of the usable time period of the body attachable unit, which are transmitted from the body attachable unit to the communication terminal.

3. The notification method according to claim 2, wherein the notification regarding the remaining usable time period of the body attachable unit is generated when a notification generation time point set at the communication terminal is reached.

4. The notification method according to claim 1, further comprising, by checking whether blood glucose data which has not been received from the body attachable unit exists before the usable time period of the body attachable unit is expired, receiving, by the communication terminal, the blood glucose data, which has not been received from the body attachable unit, from the body attachable unit.

5. The notification method according to claim 1, wherein the determining of whether the communication of the body attachable unit is disconnected comprises, if the communication terminal does not receive the blood glucose data from the body attachable unit for a set time period, determining that the communication of the body attachable unit is disconnected.

6. The notification method according to claim 5, wherein the verifying of the communication disconnection time point of the body attachable unit comprises:
   calculating the actual use time period of the body attachable unit using the time point in which the body attachable unit is activated and the communication disconnection time point of the body attachable unit; and
   verifying the communication disconnection time point of the body attachable unit using whether the calculated actual use time period of the body attachable unit matches the usable time period of the body attachable unit.

7. The notification method according to claim 6, further comprising, if the calculated actual use time period of the body attachable unit does not match the usable time period of the body attachable unit, transmitting, from the server to the communication terminal, a notification indicating that blood glucose data which has not been received from the body attachable unit exists.

8. The notification method according to claim 7, further comprising, if the notification indicating that the blood glucose data which has not been received from the body attachable unit exists is transmitted from the server to the communication terminal, reconnecting, by the communication terminal, communication with the body attachable unit and receiving blood glucose data, stored at the body attachable unit, from the body attachable unit.

9. The notification method according to claim 8, further comprising, if the usable time period of the body attachable unit is expired when the communication terminal reconnects the communication with the body attachable unit, maintaining a state that power of the body attachable unit is turned off, and not measuring, by the body attachable unit, the blood glucose data.

* * * * *